United States Patent [19]

Peyman et al.

[11] 4,428,748

[45] Jan. 31, 1984

[54] COMBINED ULTRASONIC EMULSIFIER AND MECHANICAL CUTTER FOR SURGERY

[76] Inventors: Gholam A. Peyman, 1855 W. Taylor, Chicago, Ill. 60612; Notilal Raichand, 2701 W. 35th St., Oak Brook, Ill. 60522; Edward J. Murray, 9223 W. 119th St., Palos Park, Ill. 60494

[21] Appl. No.: 138,711

[22] Filed: Apr. 9, 1980

[51] Int. Cl.³ ............................................. A61B 17/20
[52] U.S. Cl. ..................................... 604/22; 128/305; 433/119
[58] Field of Search ..................... 128/24 A, 24.1, 305, 128/276, 62 A, 24 R, 908; 310/26; 433/118, 119, 122; 318/118, 119; 51/59 SS; 604/22, 46

[56] References Cited

U.S. PATENT DOCUMENTS

| | | | |
|---|---|---|---|
| 3,526,219 | 9/1970 | Balamuth | 128/305 |
| 3,589,363 | 6/1971 | Banko et al. | 128/24 A |
| 3,628,094 | 12/1971 | Penfield et al. | 128/908 |
| 3,994,297 | 11/1976 | Kopf | 128/305 |
| 4,011,869 | 3/1977 | Seiler, Jr. | 128/305 |
| 4,111,207 | 9/1978 | Seiler, Jr. | 128/305 |
| 4,180,074 | 12/1979 | Murray et al. | 128/276 |

OTHER PUBLICATIONS

Safety Aspects of Electromedical Equipment 2, The Leakage Currents, Khandpur, CSIO Communications (India), vol. 3, No. 2, Apr.-Jun. 1976.

Primary Examiner—C. Fred Rosenbaum
Assistant Examiner—J. L. Kruter
Attorney, Agent, or Firm—Hill, Van Santen, Steadman & Simpson

[57] ABSTRACT

A surgical system and apparatus which includes a handpiece with an ultrasonic motor for driving a needle or other instrument with ultrasound and further including a cutting tube or rotary motor that is mounted within the needle such that the tube can cut material which passes through openings in the tube to be engaged by the tube. Irrigation and aspiration is provided and a surgeon may selectively cut with ultrasound, or with the cutting action or with both, as required. The handpiece may be combined with a built-in light source.

15 Claims, 5 Drawing Figures

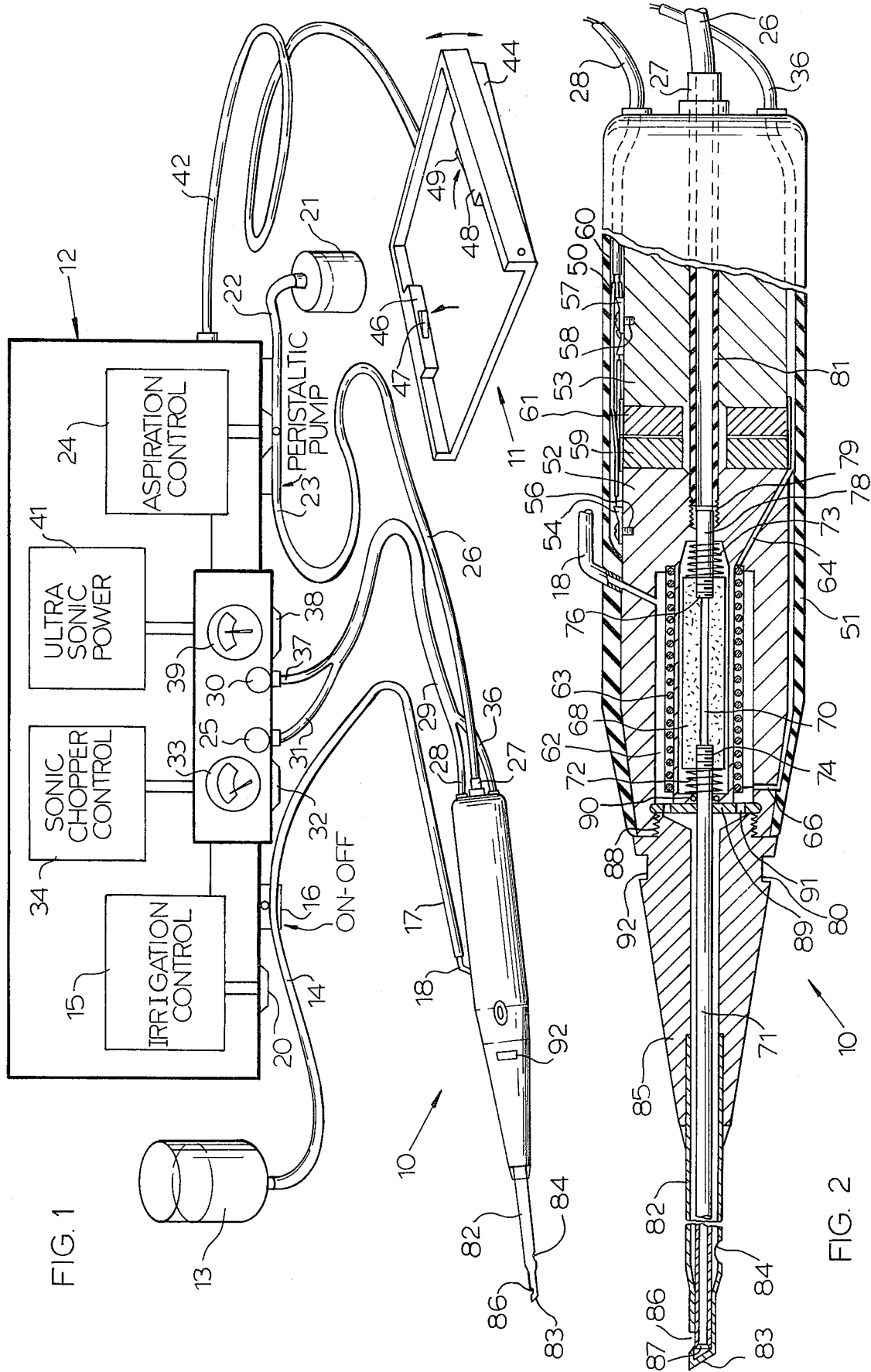

COMBINED ULTRASONIC EMULSIFIER AND MECHANICAL CUTTER FOR SURGERY

BACKGROUND OF THE INVENTION

1. Field of the Invention

Cataracts are one of the most common causes of curable blindness, and cataract surgery is one of the most common operations performed in ophthalmic practice. Conventional surgical techniques have been developed over many centuries and were until recently the main form of surgery of cataracts.

In U.S. Pat. No. 3,990,452, an advanced and improved machine for performing eye surgery with ultrasonic energy was disclosed. In prior U.S. Pat. Nos. 3,776,238 and 4,099,529, an instrument for ophthalmic surgery which consists of a hollow needle with an internal movable hollow cylinder, which was capable of cutting tissue by reciprocation, and wherein an opening was formed in the outer needle so that material could be engaged by the inner plunger so as to be sheared. These prior systems were two separate and distinct machines and handpieces used separately applying ultrasonic energy and mechanical chopping or shearing for performing cataract and vitreous removal respectively. The present invention provides a single handpiece which is compact and effective in which an instrument of unique and flexible design is provided that allows the surgeon to provide ophthalmic or other types of surgery with a single instrument which can simultaneously or separately allow the application of cutting with an ultrasonic needle or with chopping and can be used for doing such operations as iridectomy, lensectomy, vitrectomy and other related eye procedures such as cutting bands and membranes in the eye. Using the same principles this instrument can be used for diagnostic, and therapeutic purposes for other organs and tissues such as liver, intravertebral disc or brain, etc.

2. Description of the Prior Art

U.S. Pat. No. 3,990,452, which was issued on Nov. 9, 1976 discloses the use of ultrasonic energy to a hand-held instrument utilizing needles, curvettes, gouges and knives of various sorts for the removal of cataracts by fragmentation and emulsification. This device while effective for a soft cataract and vitreous did not adequately process hard cataracts or the vitreous hemorrhage preretinal membrane and bands and abscess.

A chopper is disclosed by one of the inventors of this application in U.S. Pat. No. 4,099,529 which comprises an improvement on U.S. Pat. No. 3,776,238. Such chopper comprises a chopping device in which a nested pair of hollow tubes or needles with an opening formed in the outer tube provides vibration of the tubes relative to each other so as to cause a shearing action to take place at a small slot near the end of the outer tube thereby chopping or nibbling away the vitreous strands and tissue. This machine has been in use satisfactorily since its invention.

There are several diseases of the eye which make it necessary to sever the vitreous strands which are long chain protein molecules (collegens) and then require that the resulting debris be removed. The vitreous is not a fluid, rather a gel with a matrix of long, thin filaments. The whole vitreous is a continuous body. Aspiration of vitreous is not safe because of this and also because of an anatomical attachment of the retina. The machines which work by suction or aspiration alone, are not effective in dealing with vitreous pathology. Since these strands are extremely tough and difficult to cut, simple severance with a scalpel is not possible and resort must be made to a more sophisticated shearing action.

Several methods have been suggested for doing this and, indeed, utilized, with the most obvious being the use of micro-scissors. A rotary type cutting with infusiourial and aspirational extractions additions for removal of the chopped vitreous tissue is known. Conor O'Mally and Ralph Hainz Sr. in their U.S. Pat. No. 3,815,604 (June 1972) also show an instrument of the dual tubular, nested type typical of the genre for cutting vitreous strands and membranes, which has proved quite effective heretofor, but which are subject to the usual limitations of this entire group of tubular shearing choppers. Instead of tubular shearing choppers, a rotary mechanism can be used to cut tissue.

The presently available phacoemulsificier uses limbal approach for removal of cataracts. This method has a very high complication rate. Not only is this system incapable of handling vitreous, but also lens material that falls into the vitreous cannot be removed by this system. Similarly, the automated vitreous instruments have shortcomings. They cannot cut and remove hard lens materials.

SUMMARY OF THE INVENTION

The inventors have become aware of the shortcomings or the presently available systems, the separate machines of the prior art, and have discovered that combining the two techniques yields an excellent system which has the capacity to deal with hard tissue more effectively. There is a need for both improved method and apparatus in ophthalmic surgery and the present invention comprises a radically new approach to the solution of the total surgical need—it provides a single medical machine that incorporates the best and most desirable features of the two separate machines in an efficient manner. The single medical machine exhibits all the safe and effective features of the two separate machines now utilized, and will more effectively remove hard cataracts than either prior machine alone and will deal effectively with vitreous pathology.

The present invention is for a specific surgical need and, for example, might use 40,000 cycles per second frequency for the ultrasonic energy which drives the outer needle, while superimposed on the inner needle is a lower frequency of 5–100 cycles per second of sonic energy. The ultrasonic energy is used for fragmentation of the hard mass of tissue, for example, the lens of the eye, and the sonic energy is used for providing the chopping action. The fragmentation and the cutting actions occur simultaneously. Practical operating features such as irrigation, aspiration, chopping and application of ultrasonic fragmentation energy to the operating site may be applied as required in total or severally by the surgeon.

Other objects, features and advantages of the present invention will become apparent from the following preferred embodiments thereof taken in conjunction with the accompanying drawings, although variations and modifications may be effected without departing from the spirit and scope of the novel concepts of the disclosure.

BRIEF DESCRIPTION OF THE DRAWINGS

FIG. 1 illustrates the complete system in which the improved operating handpiece of the present invention is used;

FIG. 2 comprises a longitudinal sectional view through the operating handpiece of the invention;

DESCRIPTION OF THE PREFERRED EMBODIMENTS

Figure 3:
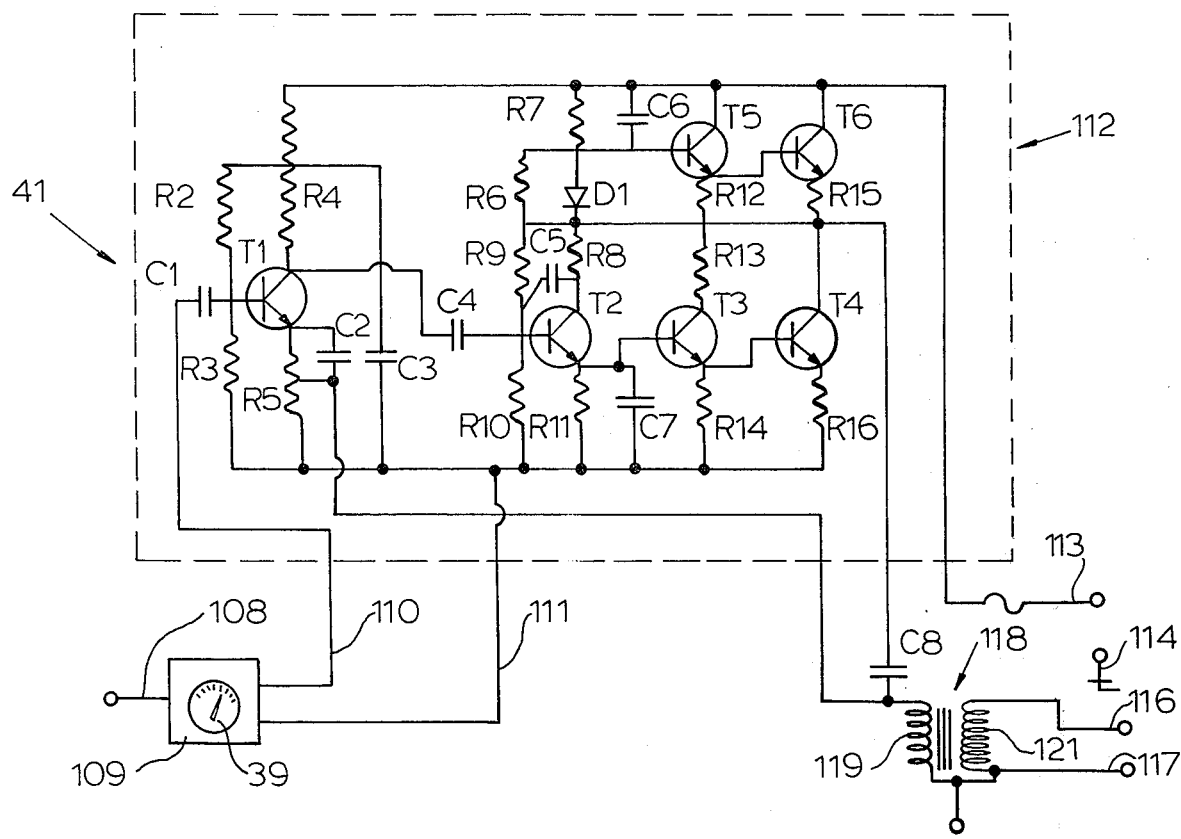
FIG. 3 illustrates the electrical schematic for the oscillating drive circuit of the ultrasonic source for the operating handpiece.

FIG. 1 illustrates the several parts of the invention which includes a handpiece 10 having an operating needle 82 with a tip 83, a foot control switch 11 and a control central 12. Fluid for irrigation is applied to the handpiece 10 from a supply bottle 13, which is connected to a tube 14 which passes through an on-off valve 16 and then through a tube 17 to a coupling 18 on the handpiece 10 for supplying irrigation fluid to the operating site. An irrigation control 15 is provided with a knob 20 for also controlling the irrigation flow inside the handpiece.

Aspiration is provided by a collecting bottle 21 which receives the aspirated fluid from a tube 22 which is supplied from a peristaltic pump 23 that is connected to a tube 26. Tube 26 is connected to a suitable coupling 27 which provides aspiration from the handpiece 10. An aspiration control 24 is connected to the peristaltic pump 23 and the foot switch 11 has an aspiration control switch 48 with an on-off contact button 49 that can be controlled by the surgeon's foot. The foot control 11 also has an irrigation control switch 46 which can be controlled by the on-off switch contact button 47 by the surgeon's foot. By pivoting down on the foot plate 43 relative to the base 44, a momentary control switch may be actuated to turn on the ultrasonic power as needed. The various electrical cables from the foot control 11 are housed in a cable 42, connected to the control unit 12.

Ultrasonic power is applied to the outside needle 82 from an ultrasonic power source 41 that has an output power meter 39 and a control knob 38 and through a cable 37 which connects to cable 28, which has two conductors 50 and 60 connected to the ultrasonic motor to drive the needle 82. Sonic chopper power is supplied from a sonic power generator 34 which provides an output through an indicating meter 33 and has a control knob 32 through leads 31, through cable 29 to cable 36 which carries conductors 64 and 66 which are connected to drive the hollow needle or plunger 71 contained inside the needle 82 and the handpiece 10 to provide chopper power. There is no direct electrical connection to the tip of the instrument, so there is no electrical shock hazard.

FIG. 2 comprises a transverse sectional view through the handpiece 10. The handpiece 10 has an outer plastic coating 51 about the cylindrical body which comprises two cylindrical portions 52 and 53 separated by piezoelectric disc members 59 and 61 to form the ultrasonic motor. A set screw 56 attaches conductor 60 to cylindrical portion 52 and a set screw 58 attaches electrical conductor 50 to cylindrical portion 53. The conductors 50 and 60 pass through cables 28 and 29 and connect to cable 37 through which the ultrasonic power is applied. The tip could be a fixed part of the handpiece as in a disposable hand unit. A tapered horn portion 85 is threadedly received into threads 88 at the front end of the cylindrical portion 52 of the handpiece and the outer needle 82 is mounted in the end of the horn portion 85 and is formed with a point 83 and a chopper and aspiration opening 86 closely adjacent the end. An irrigating opening 84 is also formed in the outer needle 82. Flats 80 and 92 are provided in the horn 85, so as to accept a wrench for tightening the horn 85 into the handpiece 10. A hollow inner needle 71 is mounted concentrically within the outer needle 82 and is oscillated back and forth so that its end 87 performs a shearing action as the inner needle is oscillated so as to cut tissue which extends into the opening 86 of the outer needle in the manner as previously described in U.S. Pat. Nos. 4,099,529 and 3,776,238.

The inner end of inner needle 71 is threadably received in one end of powdered iron core 68, which is formed with a central opening 70 and which is mounted in a cylindrical opening 62 formed in the cylindrical body member 52. A circular diaphragm 89 formed with openings 91 is mounted at the end of the opening 62 and has a central opening through which the inner needle 71 extends and an O-ring seal 90 forms a fluid seal between the needle 71 as well as forming a needle guide. A pair of springs 72 and 73 are respectively mounted at either end of the power core 68 to bias it generally toward the center of the cavity 62 and an energizing coil 63 of generally cylindrical form fits about the iron core 68 within the cavity 62 and has input leads 64 and 66 which pass through cable 36, 29, and 31 to the sonic chopper power generator 34.

The springs 72 and 73 may be made of phosphor bronze material and may be helical in shape. When the core 68 is driven by the alternating current in the winding 63 which produces a magnetic field the springs maintain pressure on both ends of the coil so that it will oscillate back and forth about a centered position, thus causing the inner needle 71 to chop tissue with its sharp outer end 87.

A flexible supply tube 78 is threadedly received in the opposite end 76 of the core 68 and extends through the spring 73 and connects to the central bolt/tube 81 through a neckdown section 79. The tube 81 passes through the coupling 27 and connects to the tube 26, thereby providing the aspiration passage.

This structure can be arranged as in a vitrophage or in a similar fashion (conceal the ocular tubular for infusion). Also the irrigation could be through a separate tubing inside the eye or other organ. The irrigating fluid passes from the supply bottle 13 through the tubes 14, 17 and connection 18 on the handpiece, through a hollow bore which joins with the cavity 62 such that the irrigation fluid bathes the coil 63 to cool it, but does not actually short out the coil 63. The irrigation fluid passes from the cavity 62 through the openings 91 formed in the diaphragm 89 then through the passage surrounding the inner needle 71 through the horn 87 and out the opening 84 of the outer needle 82.

The aspiration fluid and debris passes through the opening 86 then through the center of the inner hollow needle 71, through the opening 70 of the core 68 then through tube 78, through bolt/tube 81 to the aspirating tube 26. The cutting opening in the outer needle 82 can be round, oval, angled, notched or a combination thereof.

The system could have a built-in light source, e.g., fiberoptic pipe, for illumination or the light source could be separate.

The transition horn 85 and the needle structure is constructed as an exponential extension as described in U.S. Pat. No. 3,990,452 to provide a desirable match for the high frequency mechanical energy. The transition horn 85 is connected to the body at a vibratory null point so as to prevent the adapter or horn from unscrewing itself from the horn when in use.

The outer needle 82 is mounted in a deep counter bore which is formed in the end of the horn 85. Since it is vibrated at an ultrasonic frequency as, for example, at 40,000 times per second, the needle must be brazed to the adapter with special brazing compounds. Also, there must not be any voids or cavities in the resonating structure or most of the high frequency energy will be lost.

The inner needle 71 may have its end 87 formed with an inverse taper end sharpened so as to facilitate superior shearing and cutting as its moves past the hole 86 of the outer tube 82.

FIG. 3 illustrates a high wattage small size power amplifier with a berylium heat sink such as manufactured by the Sangem Electric Co., Ltd. An oscillator 109 is controlled by the knob 30 shown on the front panel of the control 12 illustrated in FIG. 1 and supplies an output through terminals 110 and 111 to an amplifier comprising the transistors T1, T2, T3 and T4, T5, and T6. The output transformer 118 is connected to the output of the amplifier 112 and supplies an output power on terminals 116 and 117 through cable 37 so as to drive the ultrasonic motor. The output transformer 118 may be a plug-in type, which may be interchangeable to match the instrument being used at the particular time such as a chopper, a needle or any of several varieties of knives. An oscillating system could be used, or a rotary system could be substituted, depending upon the surgery to be performed.

Figure 4:
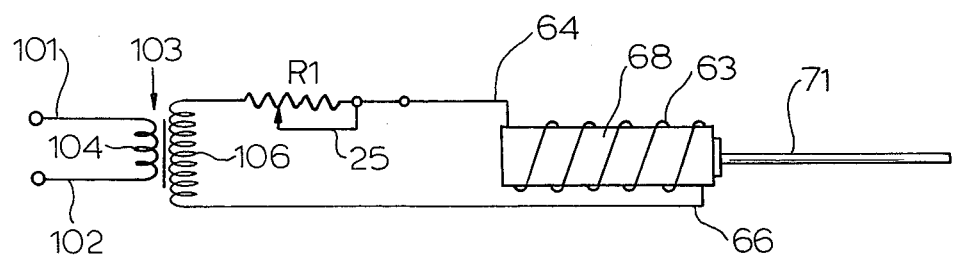
FIG. 4 is an electrical schematic illustrating the simplified sonic drive control for the operating handpiece.

FIG. 4 illustrates one type of driver for the sonic chopper which drives the core 68. 60 cycle power is applied to the terminals 101, 102 and applied across the primary 104 of the transformer 103. The secondary 106 is connected through the potentiometer R1 to the leads 64 and 66 of the coil 63. The wiper contact of the potentiometer R1 is controlled by a knob 25 so as to adjust the drive to the chopper. Of course, the rate of driving the chopper can be varied from 50 to 200 cycles if desired by varying the input frequency to the terminals 101 and 102, with an appropriate sonic oscillator.

In use, the surgeon can selectively apply irrigation fluid to the handpiece by closing the switch 47 so that fluid passes through the tube 17 and through the handpiece outer opening 84 to the opening site. Aspiration can be controlled with the switch 48 which operates the peristaltic pump 23, such that aspiration is produced through the opening 86, through the central opening of the inner needle 71, through the passage 70, tube 78, bolt/tube 81 and tube 26 and 22 to the collection container 21.

When the surgeon desires ultrasonic power, he can apply power to the ultrasonic motor through leads 54 and 57, thereby driving the outer needle 82 so as to provide ultrasonic fragmenting with the radiating end 83 of the needle 82.

If the surgeon desires to chop with the end 87 of the inner needle 71, he applies power to the coil 63 which drives the needle 71 thus causing chopping and cutting of material through the opening 86.

It is to be realized that the surgeon may simultaneously utilize ultrasonic power to fragment with the needle 82 as well as sonic chopper power to cut with the chopping action of the inner needle 71 or he may elect to use only one of the two cutting modes.

The surgeon may also selectively irrigate and aspirate as he desires.

Although the present invention provides for irrigation and/or aspiration through the concentric needles of the handpiece, it is to be realized that a separate irrigating and/or irrigation needle could be utilized during surgery, as described in U.S. Pat. No. 3,990,452.

Figure 5:
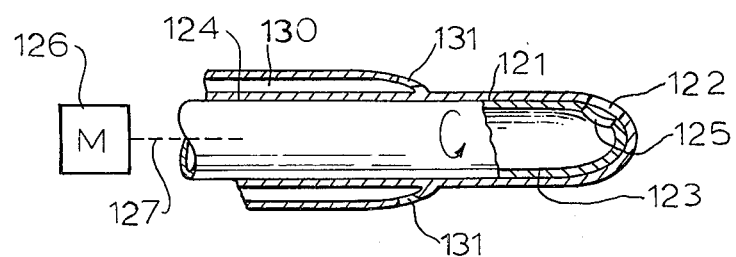
FIG. 5 is an enlarged detailed view of a modification of the invention.

FIG. 5 illustrates a modification of the invention wherein a rotary or oscillating chopper comprising a tube 123 with an opening 125 is mounted in an outer tube 121 and has an opening 122 which at times mates with opening 125 so that cutting can occur as openings 122 and 125 move relative to each other. A motor 126 is connected to tube 123 by shaft 127 to rotate or oscillate it. The outer tube 101 has an inner partition wall 124 and an irrigating cavity 130 is formed by the wall 124 and outer tube 130 and openings 131 are provided to supply irrigating fluid to the operating site. Aspiration can also be applied to tube 123 so as to aspirate the excised matter to remove it. Ultrasonic energy would also be applied to the tubes 121 and 131 as in the first embodiment so that simultaneous or alternate cutting by ultrasonic or a mechanical power can be utilized.

Although the invention has been described with respect to preferred embodiments, it is not to be so limited as changes and modifications can be made which are within the full intended scope of the invention as defined by the appended claims.

We claim as our invention:

1. An ophthalmic medical cutting instrument comprising a handpiece, an outer tube means, an inner tube means coaxially mounted in said outer tube means, a remote connected ultrasonic generator, an ultrasonic motor connected to said ultrasonic generator means and mounted in said handpiece producing signals in a frequency range above 20,000 cycles per second in and through the handpiece for driving said outer tube means for vibratory fragmentation of eye tissue, a separate drive means connected to said inner tube means and mounted in said handpiece for reciprocably driving said inner tube means for shearing eye tissue, and said outer tube having a side opening so that said inner tube can shear eye tissue and said ultrasonic motor means and said separate drive means can be simultaneously or individually operated.

2. A medical instrument according to claim 1 including aspiration means connected to said handpiece to provide aspiration at the cutting site.

3. A medical instrument according to claim 2 including irrigation means for supplying irrigation fluid to said cutting site through the handpiece.

4. A medical instrument according to claim 3 wherein said irrigation means supplies fluid through said handpiece.

5. A medical instrument according to claim 4 wherein said inner tube is hollow and aspiration is accomplished through said side opening and through said hollow inner tube.

6. A medical instrument according to claim 5 wherein said outer tube is formed with a second side opening through which said irrigation fluid passes after traveling through a passage between the outer surface of said inner tube and the inner surface of said outer tube.

7. A medical instrument according to claim 6 wherein said aspiration means includes a suction pump and a collection container connected with a suction tube to said hollow inner tube.

8. A medical instrument according to claim 7 including a control means connected to said pump to control the aspiration.

9. A medical instrument according to claim 8 wherein said irrigation means includes a supply container and a supply tube connected to said passage between the outer surface of said inner tube and the inner surface of said outer tube.

10. A medical instrument according to claim 9 including an on-off valve in said supply line.

11. A medical instrument according to claim 10 including a foot control having a first switch connected to control said valve, a second switch for controlling said pump and a third switch for controlling said ultrasonic generator.

12. A medical instrument according to claim 11 wherein said drive means is mounted directly in an ultrasonic transformation horn portion of the ultrasonic motor.

13. A medical instrument according to claim 12 wherein the operating tool is removable from said handpiece.

14. A medical instrument according to claim 13 wherein said separate ultrasonic generator and said drive means including means for changing the applied frequencies, and their amplitude to match variations in the chopper, and vibrating tool.

15. A medical instrument according to claim 14 including safety means to turn off said generators if they lose their grounds or the ground to the patient.

* * * * *